United States Patent
Pan et al.

(10) Patent No.: US 8,431,761 B2
(45) Date of Patent: *Apr. 30, 2013

(54) HYDROCARBON DEHYDROGENATION WITH ZIRCONIA

(75) Inventors: Wei Pan, Mount Prospect, IL (US);
Stephen M. Casey, Chicago, IL (US);
Bryan K. Glover, Algonquin, IL (US);
Feng Xu, Arlington Heights, IL (US)

(73) Assignee: UOP LLC, Des Plaines, IL (US)

(*) Notice: Subject to any disclaimer, the term of this patent is extended or adjusted under 35 U.S.C. 154(b) by 349 days.

This patent is subject to a terminal disclaimer.

(21) Appl. No.: 12/488,998

(22) Filed: Jun. 22, 2009

(65) Prior Publication Data

US 2009/0325784 A1 Dec. 31, 2009

Related U.S. Application Data

(60) Provisional application No. 61/076,607, filed on Jun. 27, 2008.

(51) Int. Cl.
*C07C 5/333* (2006.01)
(52) U.S. Cl.
USPC .......................................... 585/661; 585/654
(58) Field of Classification Search .................. 585/654, 585/661
See application file for complete search history.

(56) References Cited

U.S. PATENT DOCUMENTS

| | | | |
|---|---|---|---|
| 4,162,234 A | 7/1979 | Grasselli et al. | |
| 4,210,440 A | 7/1980 | Okada et al. | |
| 4,440,871 A | 4/1984 | Lok et al. | |
| 4,554,143 A | 11/1985 | Messina et al. | |
| 4,752,651 A | 6/1988 | Kaiser | |
| 4,793,984 A | 12/1988 | Lok et al. | |
| 4,853,197 A | 8/1989 | Wilson et al. | |
| 5,476,981 A | 12/1995 | Umansky et al. | |
| 5,712,218 A | 1/1998 | Chopin et al. | |
| 6,156,685 A | 12/2000 | Marella et al. | |
| 6,417,422 B1 | 7/2002 | Liu | |
| 6,486,370 B1 * | 11/2002 | Rende et al. | 585/444 |
| 6,576,804 B1 | 6/2003 | Heineke et al. | |
| 6,777,371 B2 | 8/2004 | Liu | |
| 6,790,431 B2 * | 9/2004 | Wang et al. | 423/651 |
| 6,858,768 B2 | 2/2005 | Budin et al. | |

(Continued)

FOREIGN PATENT DOCUMENTS

| | | |
|---|---|---|
| EP | 0 180 513 A1 | 6/1988 |
| EP | 0 557 790 A1 | 9/1993 |

(Continued)

OTHER PUBLICATIONS

PCT International Search Report and Written Opinion dated Jul. 22, 2010, PCT/US2009/048252, International Filing Date: Jun. 23, 2009.

*Primary Examiner* — Elizabeth Wood
(74) *Attorney, Agent, or Firm* — Arthur E Gooding (57) ABSTRACT

A method for obtaining an olefin is disclosed, the method comprising subjecting a paraffin to dehydrogenation in the absence of oxygen and in the presence of a catalyst comprising a crystalline substrate, to obtain an olefin. The catalyst includes an inert stabilizing agent for maintaining the catalyst crystal structure. The catalyst may be regenerated by being subjected, in air, to a temperature between about 550° C. and about 750° C., for a period of time between about 15 minutes and about 4 hours.

18 Claims, 4 Drawing Sheets

U.S. PATENT DOCUMENTS

| | | |
|---|---|---|
| 6,979,396 B2 | 12/2005 | Gillespie et al. |
| 7,015,175 B2 | 3/2006 | Vassilakis et al. |
| 7,227,049 B2 | 6/2007 | Liu |
| 2003/0040655 A1 | 2/2003 | Budin et al. |
| 2003/0208095 A1* | 11/2003 | Budin et al. ............... 585/658 |
| 2004/0068148 A1 | 4/2004 | Allison et al. |
| 2006/0094914 A1* | 5/2006 | Alerasool et al. ............ 585/444 |
| 2006/0149112 A1* | 7/2006 | Rokicki et al. ............... 585/654 |
| 2007/0043245 A1 | 2/2007 | Kaizik et al. |

FOREIGN PATENT DOCUMENTS

| | | |
|---|---|---|
| EP | 1 038 577 A1 | 12/2005 |
| JP | 6 199569 | 7/1994 |
| KR | 10-2002-0088143 | 11/2002 |
| WO | WO 2005/100248 A1 | 10/2005 |
| WO | WO 2007/008288 A1 | 1/2007 |

\* cited by examiner

HYDROCARBON DEHYDROGENATION WITH ZIRCONIA

CROSS-REFERENCE TO RELATED APPLICATIONS

This application claims priority to Provisional U.S. Application No. 61/076,607, filed Jun. 27, 2008, all of which is incorporated by reference.

FIELD OF THE INVENTION

This invention relates to the dehydrogenation of hydrocarbons. More specifically, selective dehydrogenation of paraffins using selective catalysts for the production of olefins and aromatics.

BACKGROUND OF THE INVENTION

Dehydrogenation of paraffins, particularly lower paraffins such as propane or butane, to obtain corresponding olefins is an endothermic reaction. The process is traditionally carried at high temperatures, such as between 550° C. and 650° C., and in the presence of a metal-based catalyst. Due to the high temperature, the catalyst is quickly and easily coked, and the period of time during which the catalyst is stable is limited, in some instances to minutes or even seconds.

While the stability of the catalyst can be somewhat improved by using it in a form of a fluidized bed, traditional catalytic dehydrogenation of paraffins has other drawbacks and deficiencies besides problems with stability. For example, in traditional catalytic dehydrogenation many catalysts cannot withstand many cycles of regeneration and heat integration without substantial loss of activity and selectivity. The ability of catalysts to promote selective reactions (i.e., reactions leading to the formation of the desired final product) is also limited in traditional processes, and the share of thermal, non-selective reactions (i.e., reactions leading to the formation of the products other than the desired product) is often larger then desired.

One class of non-noble metal dehydrogenation catalysts that was previously described includes molybdenum oxides on a support, e.g., $MoO_x$ on gamma-alumina or $ZrO_2$ that may have activity similar to that of platinum based catalysts, such as Oleflex™ catalysts. However, such $MoO_x/Al_2O_3$ or $MoO_x/ZrO_2$ catalysts are often characterized by poor hydrothermal stability usually leading to a quick loss of activity. Catalysts that include calcium or yttrium-stabilized $ZrO_2$ also may lose significant surface areas to coke contamination, also leading to the eventual loss of activity. In addition, in case of calcium-stabilized substrates, an inactive material $CaMoO_4$ may be formed, which is undesirable.

The above-mentioned and other drawbacks and deficiencies of traditional catalytic dehydrogenation of paraffins have not been resolved. To improve the overall efficiency of dehydrogenation, it is desirable to have catalysts possessing better activity, stability and selectivity. Ideally, thermal, non-selective reactions should be eliminated or at least substantially decreased. To achieve these ends, better catalysts are needed, particularly those that are hydrothermally stable, so that the catalysts can retain their stability and selectivity when the regenerated catalyst is subjected to high temperatures. It is also very desirable to have a catalyst that may be regenerated with a carbon burn.

SUMMARY OF THE INVENTION

This invention comprises a process for the dehydrogenation of a paraffin stream in the absence of oxygen. It has been found that the use of a catalyst without a metal deposited on the catalyst dehydrogenates paraffins with very high selectivity. The process comprises contacting the paraffin stream with a catalyst comprising zirconia, and stabilized with a metal oxide wherein the metal is selected from the group consisting of scandium, yttrium, lanthanum, cerium, actinium, calcium, magnesium, silicon, and mixtures thereof. A product stream is generated comprising olefins, and the olefins are recovered from the product stream.

Other objects, advantages and applications of the present invention will become apparent to those skilled in the art from the following detailed description and drawings.

DETAILED DESCRIPTION OF THE INVENTION

UOP has a process for converting light paraffins to polymer grade olefins. This is a flexible and highly selective process for use in converting paraffinic hydrocarbons in the range of C3 to C5 to the corresponding olefins. Currently, when catalytic processes are used for the dehydrogenation of light paraffins, the process includes use of a highly selective platinum based catalyst. The current state of understanding of catalytic dehydrogenation is that the catalyst includes a metal function for performing the dehydrogenation, where the metal is in its zero state. The preferred metals are noble metals such as platinum and palladium, but other metals are being studied and include molybdenum, tungsten and other transition metals, or silicon, and metal carbides, such as molybdenum carbide and tungsten carbide. One of the problems with the current process is the maximum through put for a single train, or series of reactors. Another problem is the reactor sensitivity to reactor fouling. The catalyst is expensive and reducing the amount of regeneration of the catalyst increases productivity.

The process comprises passing a paraffinic feedstock through a plurality of reactors in series, while also passing a catalyst through the reactors, thereby generating an intermediate process stream passing between reactors. Because the process is endothermic, the intermediate process stream comprising the paraffins and olefins is heated at intermediate stages between reactors. The catalyst, after passing through the plurality of reactors, is regenerated in a continuous catalyst regeneration section. This process is described in U.S. Pat. No. 6,969,469, issued on Nov. 29, 2005, and is incorporated by reference in its entirety.

It was unexpectedly found that yttria-stabilized $ZrO_2$ (zirconia) has been found to give very high propylene selectivity, that was very nearly equal to a commercial based catalyst, and better than a Mo catalyst for $C_3$ dehydrogenation, with activity roughly 40% of commercial catalyst. The zirconia was essentially free of all metals that one skilled in the art would use, or try, for the dehydrogenation process. This is contrary to what one of ordinary skill would look for, as a catalyst for dehydrogenation uses a metal deposited on a support which provides the metal function for the catalytic dehydrogenation. However, the zirconia could contain minute amounts of impurities that occur with any process of creating a material. Zirconia is a crystal with an average pore size of 17 nm, and an average area in the range of 40-50 m²/gm. Although the zirconia was less active, it offset the lower activity by being more selective and resulted in a high quality product stream. The yttria stabilization enhances the activity substantially over $ZrO_2$ only.

The use of platinum (Pt) on a support for catalytic dehydrogenation is well known, and commercially performed. However, it was found that zirconia, by itself, as shown in Table 1, was an effective catalyst which ran counter to what is known in the art, or that one needed a metal from Group VI (IUPAC 6) or Group VIII (IUPAC 9-10) on an inorganic oxide support.

TABLE 1

Results of Pt on zirconia and zirconia

| Sample | Temp, C. | WHSV | Propane conv., mole % | propylene sel., mole % |
|---|---|---|---|---|
| ZrO2 | 590 | 1.0 | 11.3 | 96.7 |
| ZrO2 | 620 | 1.0 | 19.2 | 93.3 |
| 0.117 wt % Pt/ZrO2 | 590 | 1.0 | 11.3 | 96.7 |
| 0.117 wt % Pt/ZrO2 | 620 | 1.0 | 18.8 | 93.5 |

The use of zirconia for the catalyst can include impurities, but the dehydrogenation conversion due to the zirconia is greater than 50% of the conversion, and preferably the dehydrogenation conversion due to the zirconia is greater than 80% of the conversion. For example, if the total conversion is about 40%, and the zirconia contribution is 80% of the total conversion, then the zirconia contributed to 32% of the conversion. The selectivity for the new catalyst is also high in that the dehydrogenation selectivity due to the zirconia is greater than 80% of the selectivity, and preferably greater than 90% of the selectivity.

One embodiment of this invention is to use the zirconia catalyst for short contact times, with the catalyst being regenerated on a continuous basis using continuous catalyst processing technology. The process comprises contacting a paraffin rich stream in the absence of oxygen with the zirconia catalyst for a contact time of less than 2 hours, thereby generating a product stream comprising olefins and then recovering the olefins. The process can used with transport reactors, which are common in hydrocarbon processing. In a transport reactor, the catalyst bed moves through the reactor when the catalyst contacts the hydrocarbon feedstream. This is different from fixed bed reactors where the catalyst doesn't move, or ebullated bed reactors where the catalyst particles circulate within the reactor, but are not carried out of the reactor. In a transport reactor, the catalyst is carried through the reactor by the reactants passing through the reactor. Although the general direction for a transport reactor is in the upward direction, a riser reactor, it can also be downward, horizontal, or at some angle between vertical and horizontal. Fluidized bed reactors are also possible where the catalyst can have a residence time within the reactor, but is carried out at a different rate than the effluent stream. The catalyst would be withdrawn continuously from the reactor, and regenerated in a regeneration unit. One type of regeneration is to burn off carbon by exposing the catalyst to an oxidizing environment, such as air or oxygen, at a temperature between 450° C. and 750° C. for a period of time between 15 minutes and 4 hours. The regeneration is for a preferred time of between 5 minutes and 3 hours, with a more preferred time between 15 minutes and 1 hour.

The use of an inorganic refractory oxide is unexpected, because prior results show that the usual inorganic refractory oxides show little or no activity, and over time any activity that is exhibited decreases to zero, thus leading to the conclusion that inorganic oxides by themselves would not be effective catalysts.

During the process of dehydrogenation of paraffins, the catalyst accrues a coke buildup over time. The coke buildup eventually adversely affects the catalyst performance and the catalyst needs to be regenerated. The catalyst is cycled through a continuous catalyst regenerator as part of the system for the paraffin dehydrogenation. Simple air-burn regeneration returns fresh catalyst performance. The regeneration can take place at ambient pressure using air, or can be at higher pressures using air, or another oxidation agent, such as oxygen, although air is preferred. Severe hydrothermal treatment tests show that surface area loss gives lower activity, but selectivity remains high or higher. The high density of the zirconia system could allow a dual-density catalyst-heat carrier system, in which an inert heat carrier could be recirculated more rapidly than the catalyst in a back-mixed fluidized bed system, to take advantage of a high heat capacity and to allow the catalyst to remain in the reactor for an optimized time, to reduce regeneration frequency.

The synthesis of zeolites of the present invention can be formed by hydrothermal crystallization from a reaction mixture containing the desired amounts of silica and alumina and a templating agent. Zeolitic synthesis processes are known in the art, and can be found in U.S. Pat. No. 4,554,143; U.S. Pat. No. 4,440,871; U.S. Pat. No. 4,853,197; U.S. Pat. No. 4,793,984; U.S. Pat. No. 4,752,651 and U.S. Pat. No. 4,310,440, all of which are incorporated by reference.

In another embodiment, the zirconia or metal oxide stabilized zirconia includes alumina. The alumina is added to increase the acidity of the zirconia and is added in an amount between 0.001 wt. % and 8 wt. %. In an alternative to alumina, aluminum chloride is added to the zirconia, or the metal oxide stabilized zirconia.

The present invention is for a non-oxidative dehydrogenation of hydrocarbons in the $C_2$ to $C_{20}$ range for branched or linear paraffins, and the $C_3$ to $C_{20}$ cycloparaffins. The dehydrogenation process uses zirconia without any metal function for the dehydrogenation process in a non-oxidative environment. The hydrocarbon comprising a paraffin stream is contacted with the zirconia at reaction conditions in a fluidized bed reactor system, thereby generating a product stream comprising olefins. The fluidized bed reactor system can include transport reactors, such as riser reactors where the catalyst and process stream flow through the reactors during the process. The dehydrogenation reaction conditions include a temperature between about 200° C. and about 650° C., and a pressure between 100 kPa and 10 MPa. A preferred temperature range is between 500° C. and about 650° C., with a more preferred range between 600° C. and about 650° C. A preferred pressure is between 100 kpa and 2 MPa, with a more preferred pressure between 100 kPa and 500 kPa.

Figure 4:
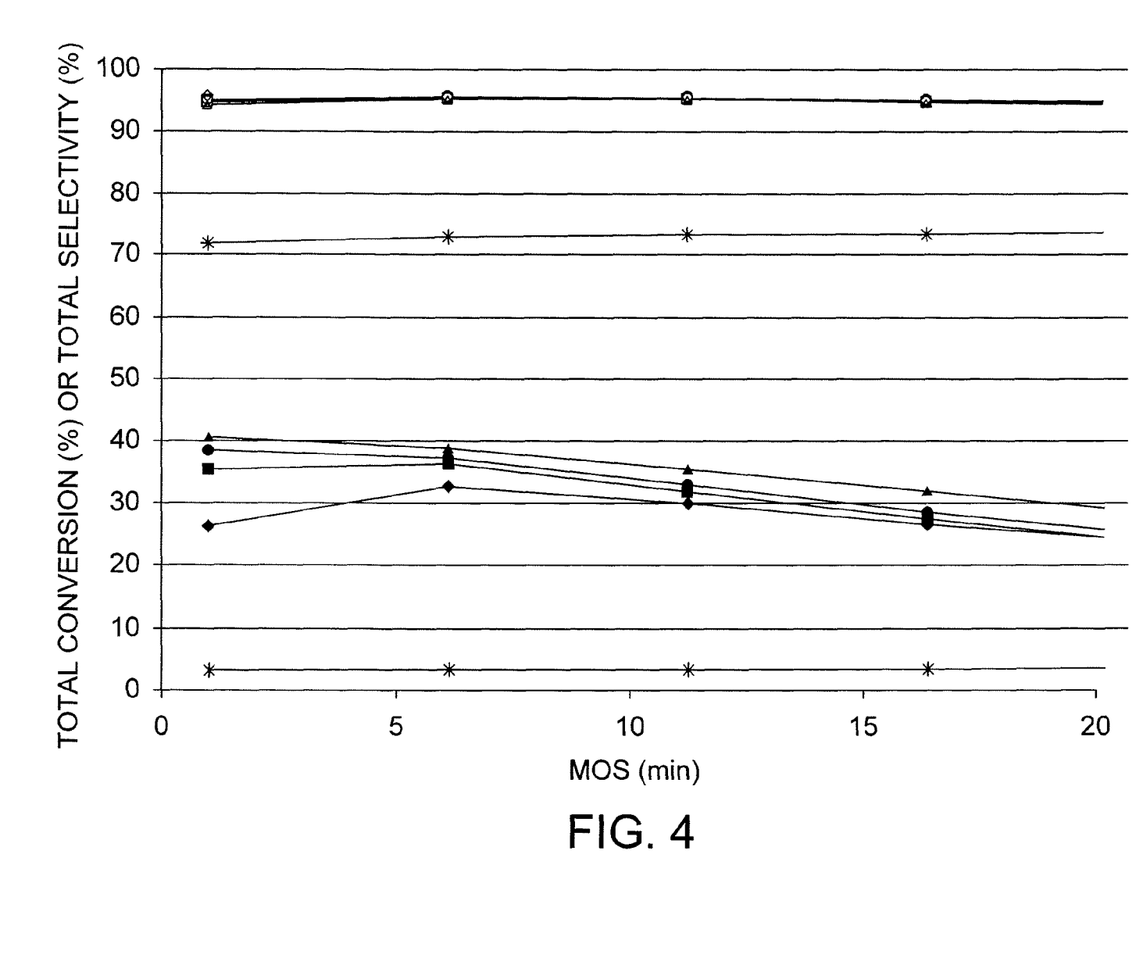
FIG. 4 shows the conversion and selectivity of the dehydrogenation with respect to moisture content.

The present catalyst can be operated under low moisture content as shown in FIG. 4, with a moisture content below 3000 ppm water, a preferred moisture content below 1000 ppm, and a more preferred moisture content below 200 ppm. The reaction can be carried out under completely arid conditions. The process further comprises a weighted hourly space velocity (WHSV) is between 0.1 $hr^{-1}$ and 20 $hr^{-1}$, with a preferred WHSV of between 0.5 $hr^{-1}$ and 10 $hr^{-1}$. The reaction conditions for the test include operating at atmospheric pressure, with a 0.5 hydrogen/hydrocarbon ratio, at 620° C., in a quartz reactor. The equilibrium is at 47%, while the tests show the results for increasing amounts of water from dry (triangle symbols), to 10-30 ppm water (circle symbols), 200 ppm water (square symbols), 800 ppm water (diamond symbols), and 3000 ppm water (stars). The conversion is shown with solid symbols, while the selectivity is shown with open symbols.

The process is endothermic, and the hydrocarbon feedstream is heated before passing to the reactor. The feedstock and catalyst travel through the reactor co-currently and the catalyst is continuously regenerated and recycled to the reactor. For multi-reactor systems with the reactors in series, the intermediate process stream is reheated with reheaters before feeding the intermediate stream to the next reactor.

The product stream is separated from the catalyst, and the catalyst is regenerated, with the product stream directed to a separation process for the recovery of olefins. The product stream separation can include methods known to those skilled in the art, and include processes such as distillation, adsorption separation, and other known processes for separation of components in the product stream. The catalyst is directed to a regeneration unit, and can be processed through a continuous catalyst regeneration system, where the catalyst is subject to reaction conditions to remove materials, such as carbon, on the catalyst. The regeneration includes passing an oxidizing gas over the catalyst at oxidizing conditions to remove carbon buildup. The catalyst is generally regenerated using an oxidizing gas, such as air, but can include oxygen, or other oxidizing gas, at temperatures between about 450° C. and about 750° C. and subject to the oxidizing reaction for a time between about 15 minutes and about 4 hours.

The process has been tested to work on paraffinic hydrocarbons in the $C_3$ to $C_{15}$ range, and more specifically in the $C_3$ to $C_5$ range, and in particular propane, n-butane and isobutane. A very successful process exists for converting $C_3$-$C_5$ paraffins to the corresponding olefin, especially propane to propylene. However polypropylene producers are demanding larger size dehydrogenation units and current technology is limited to about 500 kMTA maximum single train size. In addition, the current design is sensitive to reactor fouling. A process using a back-mixed fluidized bed catalyst system with simple air-burn regeneration could have selectivity, cost and scale-up advantages. The current process utilizes a catalyst that has an unoxidized metal deposited on a support and the metal function performs the catalytic dehydrogenation. Currently, the metal is a platinum based catalyst, which is an expensive catalyst to produce. There are many supports which include metal oxides. Zirconia has been used as a support, but not as a catalyst by itself. It is used as a catalyst when an metal in its base state is deposited on the support, and the metal function performs the catalytic dehydrogenation.

While one embodiment of the invention is to use zirconia alone in the process of conversion to paraffins to olefins, another embodiment is to add a stabilizing component to the zirconia crystal. Zirconia alone forms a monoclinic crystal structure, while the yttria stabilized zirconia forms a tetragonal crystal structure. With the addition of a stabilizing amount of yttria, the zirconia crystal structure changed to a more stable form. In this embodiment, the catalyst is stabilized by the addition of a metal oxide, wherein the metal oxide comprises a metal selected from scandium, yttrium, lanthanum, cerium, actinium, calcium, magnesium, silicon, and mixtures thereof, and preferably the metal is selected from yttrium, scandium, lanthanum, cerium, calcium, magnesium, and mixtures thereof, and more preferably yttrium, lanthanum, cerium and mixtures thereof. In a particular embodiment, the metal oxide used for stabilization is yttria.

The addition of the stabilizing metal oxide is in an amount up to 20% by weight, and preferably between 0.001% and 15% by weight of the total catalyst weight. It is preferred that the metal oxide concentration is in an amount between 0.1% and 10% by weight, and more preferred that the amount is between 1% and 8% by weight.

The stabilized catalyst is regenerated with a simple air burn at a temperature between 450° C. and about 750° C., and can be performed at approximately 550° C.

In another embodiment, the catalyst comprises a layered catalyst having an inner core made from a first refractory inorganic component, and an outer layer made of zirconia. The zirconia can further include a stabilizing metal oxide as presented above where the metal oxide is in a concentration between 0.001 wt. % and 10 wt. % of the outer layer. The metal for the stabilizing metal oxide is selected from at least one of scandium, yttrium, lanthanum, cerium, calcium, magnesium and silicon. The first refractory inorganic component is selected from alpha alumina, theta alumina, silicon carbide, metals, cordierite, titania and mixtures thereof. The inner core can selected for its ability to carry heat into the reactor. In a preferred embodiment, the inner refractory component is cordierite. The inner core can also be treated to be made inert. The outer layer of zirconia is formed on the inner core to a thickness between 50 and 300 micrometers.

The use of a stabilized zirconia catalyst, and in particular a stabilized layered zirconia catalyst, may enable the use of the zirconia catalyst for dehydrogenation processes involving longer times, or times greater than 2 hours, and even greater than 4 hours before regeneration of the catalyst.

The zirconia is a high density catalyst system, and can allow for a dual-density process wherein a lighter heat carrier component is added. The process of dehydrogenation is endothermic and the addition of heat facilitates the reaction. By adding an inert heat carrier, the process can take advantage of the additional heat to keep the catalyst in the reactor longer for a more optimal time, and to reduce the amount of regeneration of the catalyst. Therefore, in one embodiment, the process comprises a dual-density catalyst-heat carrier system, where an inert heat carrier is added and recirculated through a fluidized bed system. The inert heat carrier is lighter than the catalyst and can be partially separated in the reactor, and passes through the fluidized bed reactor faster than the catalyst. The heat carrier is reheated and recycled to the reactor to maintain the heat in the system for facilitating the reaction.

The catalyst may comprise the active catalytic material, zirconia, and an inert binder, a filler, or both. The addition of binder and/or filler provides a desired level of mechanical strength or attrition resistance of the bound catalyst. Preferably the solid catalyst is layered wherein the molecular sieve is incorporated into an outer layer bonded to an inner core. The total amount of binder and filler material preferably contributes from about 20% to about 80% of the total catalyst weight. In addition to enhancing the catalyst strength properties, the binder and/or filler materials allow the molecular sieve crystallite powder to be bound into larger particle sizes suitable for commercial catalytic processes. The molecular sieve/binder composite may be formed into a wide variety of shapes including, for example, extrudates, spheres, pills, and the like.

The binder and/or filler material is often, to some extent, porous in nature and may or may not be effective to promote the desired reactions through, for example, the provision of acid sites. The binder and filler materials may also promote reaction of the feed stream to the desired product or products relative to the catalyst. Examples of preferred binder materials include, but are not limited to alumina, silica, aluminum phosphate, silica-alumina, titania, and mixtures thereof. Filler materials can include, for example, synthetic and naturally occurring substances such as clays, metal oxides, silicas, aluminas, silica-aluminas, and mixtures thereof. In referring to the types of binders and fillers that may be used, it should be noted that the term silica-alumina does not mean a physical mixture of silica and alumina but means an acidic and amorphous material that has been cogelled or coprecipitated. In this respect, it is possible to form other cogelled or coprecipitated amorphous materials that will also be effective as either binder or filler materials. These include silica-magnesias, silica-thorias, silica-berylias, silica-titanias, silica-alumina-thorias, aluminophosphates, mixtures of these, and the like. Preferably, the filler is a clay, since clays are known to be essentially inert under a wide range of reaction conditions. Suitable clays include commercially available products such as kaolin, kaolinite, montmorillonite, saponite, and bentonite. These clays can be used as mined in their natural state, or they may also be employed in highly active forms, typically activated by an acid treatment procedure.

The process is well suited to a back-mixed fluidized bed reactor. While not being constrained by any particular theory, it is believed that the catalyst circulation rate is dictated by the required heat input into the reactor to drive the endothermic reaction or the activity of the catalyst. For a large reactor system, such as one used in the production of one million metric tons per year, the calculation of heat requirements results in a catalyst residence time on the order of 2 minutes. This is shorter than the useful time the catalyst should spend in the reactor. The catalyst is stable at the reactor conditions for 20 to 30 minutes and the selectivity improves over time. Therefore, it is desirable to increase the residence time of the catalyst in the reactor. This can be performed by using a dual-density system to add in an inert component that carries heat into the reactor, but passes through the reactor faster than the catalyst, such as using an alumina or aluminum beads. Using the density differences in the densities of zirconia and the second heat carrier, a separation mechanism is used to remove the heat carrier medium at a faster rate from the catalyst in the reactor. The heat carrier medium is then reheated outside the reactor and recycled back into the reactor system.

Figure 1:
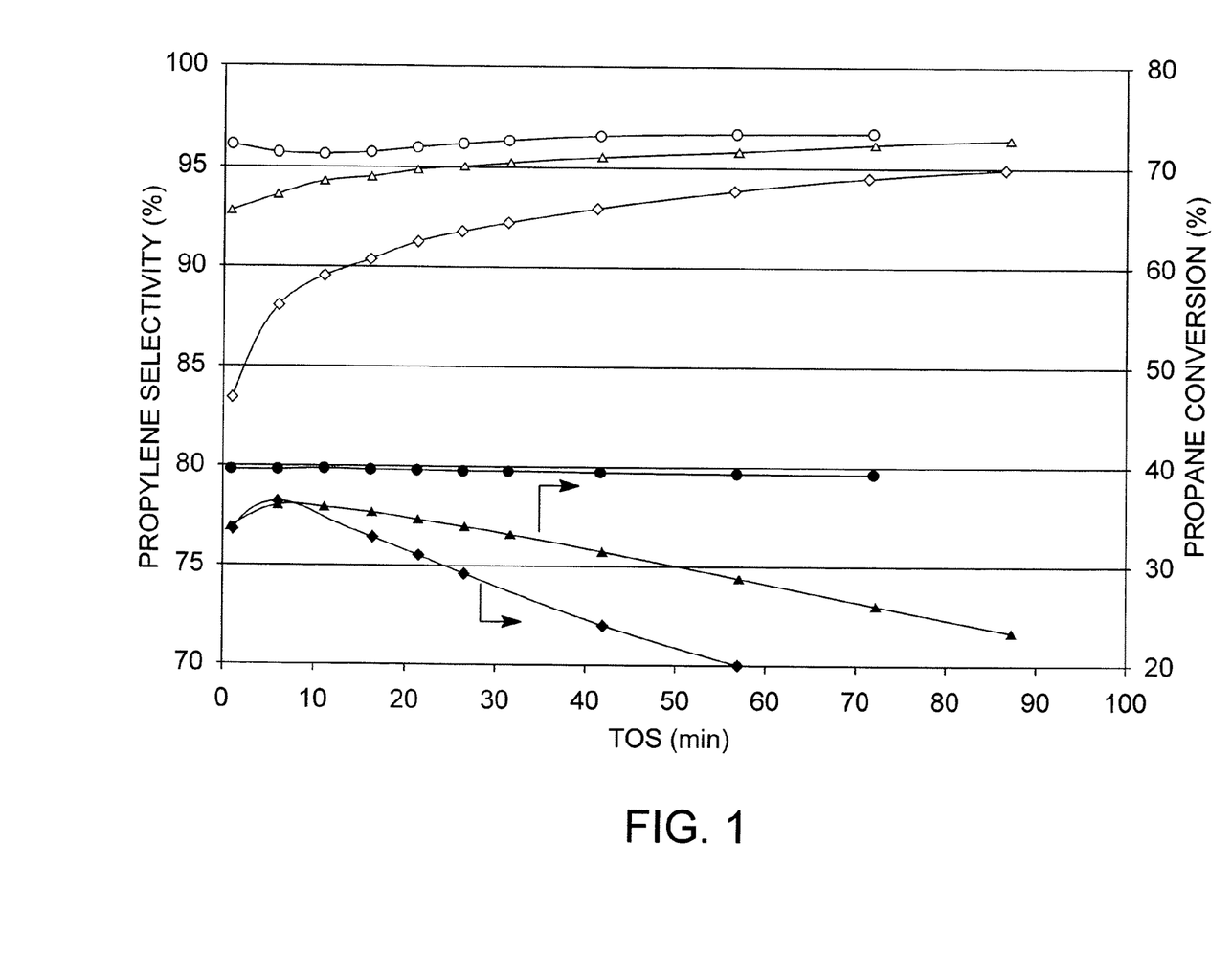
FIG. 1 shows the conversion and selectivity of yttria stabilized zirconia relative to molybdenum on yttria stabilized zirconia and a commercial dehydrogenation catalyst.

FIG. 1 shows a comparison of the selectivity and conversion of the zirconia as a catalyst when comparing with a commercial catalyst, which is a platinum catalyst on a support, and with a molybdenum catalyst on a zirconia support. The commercial catalyst is represented by circles, the zirconia catalyst with yttria for stabilization is shown with triangles and the 1% Mo catalyst on zirconia is shown with diamonds. The conversion is shown with solid symbols, while the selectivity is shown with open symbols. One would expect the metal function of the catalyst to be predominant for the dehydrogenation reaction. The tests comprised running a hydrocarbon stream over the catalyst at 620° C. under a hydrogen atmosphere. The hydrogen to hydrocarbon ratio was 2, and the flow conditions were a liquid hourly space velocity of 3. The results show the zirconia gave much better results than the molybdenum loaded catalyst, and over time while the conversion dropped, the selectivity remained high, and approached the selectivity of the commercial catalyst.

Figure 2:
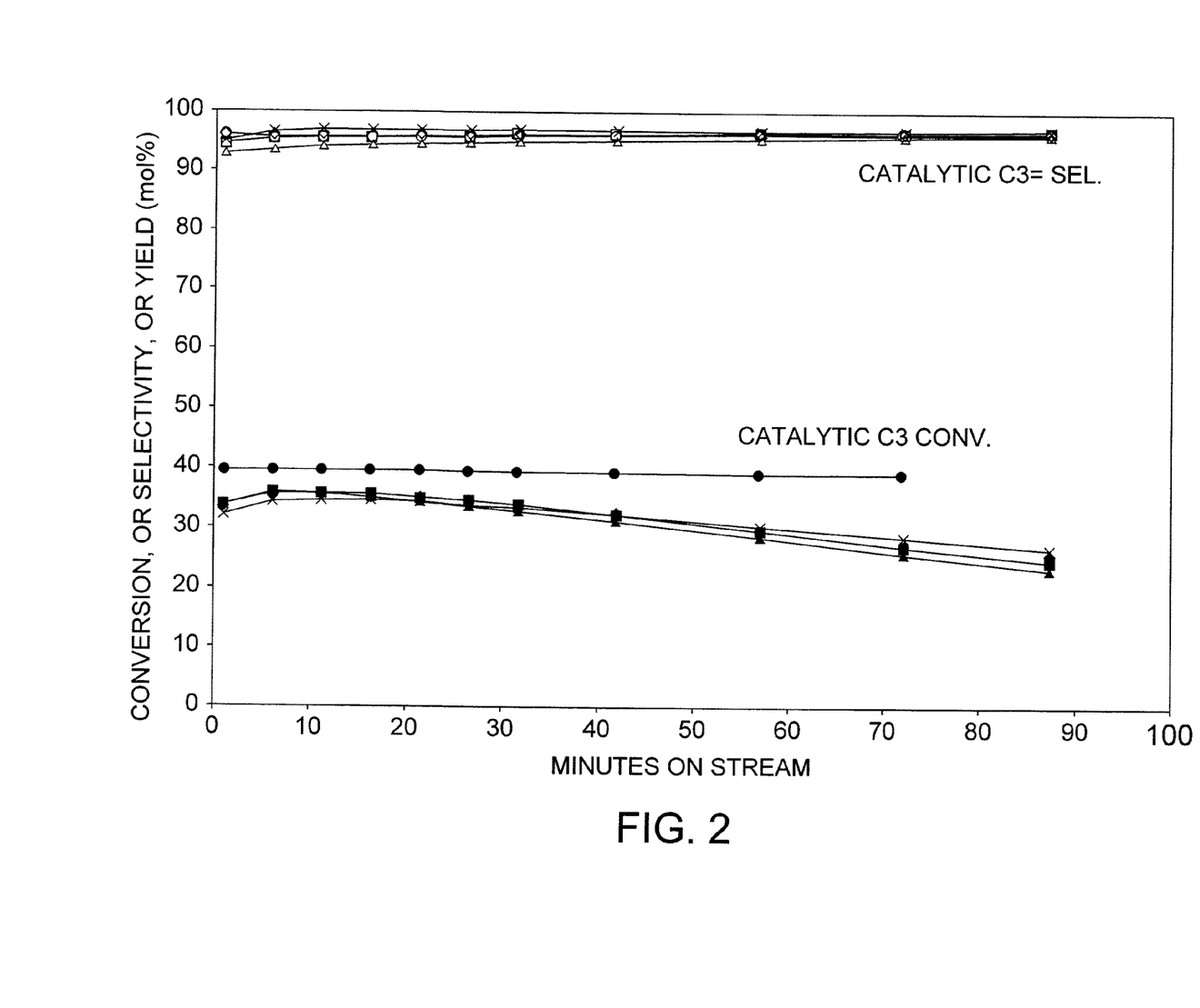
FIG. 2 shows the regenerability of the yttria stabilized zirconia.

The stability of the catalyst is shown in FIG. 2. The yttria stabilized zirconia was regenerated three times with a simple carbon burn in an oven at 550° C. for 2 hours for each regeneration. The selectivity remained high after each regeneration, and the conversion returned to approximately the same conversion levels as fresh catalyst. A comparison with the fresh commercial catalyst is also shown, where the selectivity is at the same level as the commercial catalyst, but conversion is somewhat lower than the commercial catalyst. However, the commercial catalyst is very expensive to produce and zirconia presents a significant economic advantage. The commercial catalyst is shown with circles, the yttria stabilized zirconia is shown with triangles, the first carbon burn is show with square symbols, the second carbon burn is shown with diamonds, and the third carbon burn is shown with X's. The conversion is shown with solid symbols, while the selectivity is shown with open symbols.

Figure 3:
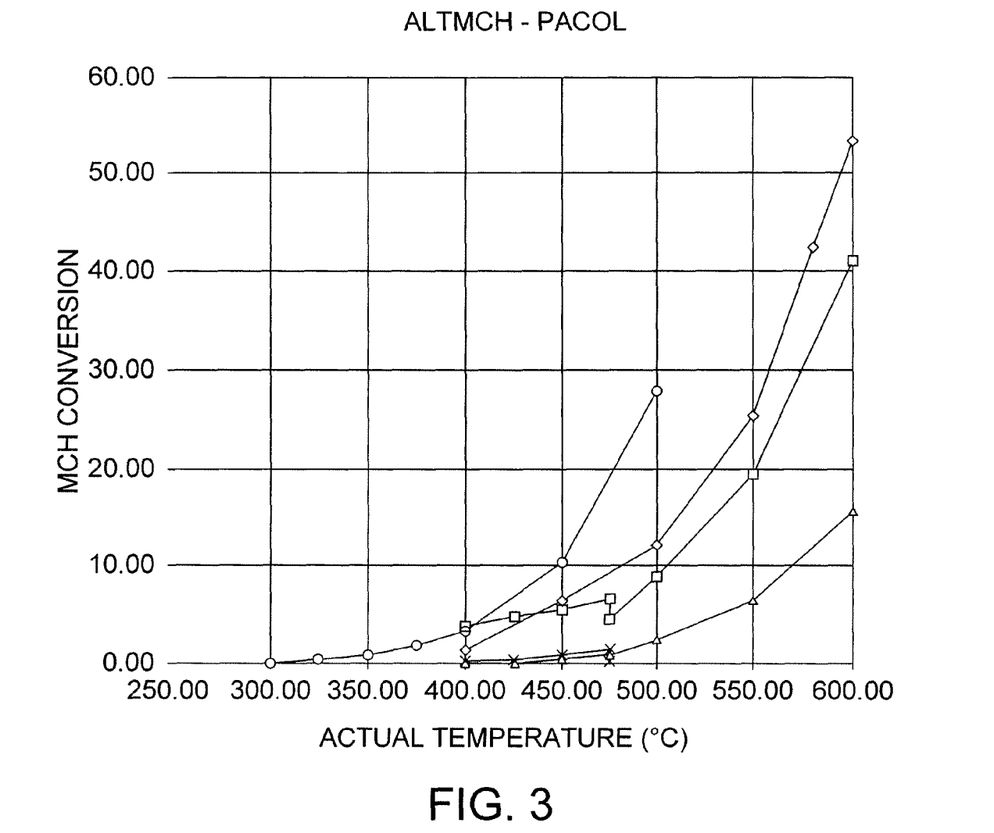
FIG. 3 shows a comparison of a commercial reference catalyst with zirconia catalysts and with zirconia/alumina catalysts.

Testing of the conversion of methyl-cyclohexane is shown in FIG. 3 for a commercial catalyst, and zirconia and mixed zirconia/alumina catalysts. The catalysts in the tests were formed using standard procedures. The zirconia/alumina catalysts were tested as 50/50 mixtures, and formed by weighing out the appropriate amounts of powdered zirconia and alumina. The powders were mixed, and the mixing continued while a 3 wt. % nitric acid solution was added for peptizing. The process continued until the mixture formed a dough-like or paste-like consistency. The mixture is then formed into pellets, where the pellets are then dried at 120° C., and then calcined at 500° C. In the figure, the commercial catalyst is shown with circles, the zirconia layered sphere is shown with diamonds, the zirconia is shown with squares, the first preparation of mixed zirconia/alumina is shown with triangles, and the second preparation of mixed zirconia/alumina is shown with X's.

While this catalyst is used for dehydrogenation, it can also be used in the reformation process, where naphthenes are dehydrogenated to form aromatics. The zirconia catalyst can also be used in combination with other more acidic catalysts in a reformation reaction zone to perform the complex chemistry in the reformation process. A normal commercial reforming catalyst comprises a platinum-group metal on a support, with platinum as the preferred metal component. The platinum may exist as an elemental metal, or as a compound such as an oxide, sulfide, halide, or oxyhalide. The preferred state is the reduced state, or as an elemental metal, and the metal comprises between 0.01 and 2 wt. % of the catalyst composite, with a preferred amount between 0.05 and 1 weight %. The supports comprise inorganic oxides such as alumina, silica, titania, magnesia, chromia, thoria, boria and mixtures thereof. The catalyst compounds also can include synthetic or natural clays and silicates, or other binding materials. The catalyst can comprise molecular sieves, both zeolitic and non-zeolitic, and may be acid treated. By combining the reforming catalyst with zirconia, the dehydrogenation function can be added with a reduction in the amount of platinum-group metal used. The zirconia can be added on top of the support, or incorporated into the support to form a porous catalytic composite.

Catalytic reforming is a complex process of competing reaction sequences. The reactions include dehydrogenation of cycloparaffins to aromatics, dehydroisomerization of alkylcyclopentanes to aromatics, dehydrocyclization of acyclic hydrocarbons to aromatics, hydrocracking of paraffins to light paraffins and olefins, dealkylation of alkylbenzenes and isomerization of paraffins. The production of light paraffins and olefins generally are undesired during the reforming process, as the reforming process is generally aimed at enhancing the products in the gasoline boiling range by increasing the octane number of the products produced in reformation. An important reaction in the reforming process is the dehydrogenation of paraffins, and especially of naphthenes to aromatics. Dehydrogenation using zirconia, or zirconia stabilized with a metal oxide as described above may increase desired products, while not increasing or performing a competing process such as catalytic hydrocracking. The reforming of a naphtha feedstock involves contacting the naphtha feedstock with a reforming catalyst. When the catalyst is zirconia, or metal oxide stabilized zirconia, the principal reforming reaction is the dehydrogenation of cycloalkanes to aromatics. The zirconia catalyst can also be combined with a second catalyst for other reforming reactions, where the second catalyst comprises an elemental metal on an inorganic refractory support, or a molecular sieve. The elemental metal can comprise a metal from Group IVA (IUPAC 14) in an amount between 0.01 wt. % and 5 wt. % of the second catalyst, and preferred metals from this group include tin, germanium, and mixtures thereof. Another combination is using the zirconia catalyst with a second catalyst having an elemental metal from the platinum group, Group VIII (IUPAC 10), on an inorganic oxide, or molecular sieve. The platinum group metal is in an amount between 0.01 wt. % and 2 wt. % of the weight of the second catalyst.

Reforming frequently requires dual functions from the catalyst, and the use of two catalysts can improve control over the extent of one process over another process within the reforming zone.

When using the zirconia in a reforming reaction zone, the reforming operating conditions include a pressure between 100 kPa (1 atm.) and 2 MPa (20 atm.), a temperature between 200° C. and 600° C., a liquid hourly space velocity between 0.1 and 40 hr$^{-1}$, and a mole ratio of hydrogen to hydrocarbon feed between 0.1 and 20.

The present invention comprises a catalyst for the dehydrogenation of hydrocarbons in the C3 to C20 range consisting essentially of: zirconia stabilized with a metal oxide selected from the group consisting of scandium, yttrium, lanthanum, cerium, calcium, magnesium, silicon, and mixtures thereof, wherein the metal oxide is in a concentration between 0.001 wt. % and 10 wt. %. The metal oxide preferably has a concentration between 0.1 wt. % and 8 wt %. In one formulation, the metal oxide is yttria with a concentration between 0.1 wt. % and 8 wt. %. The catalyst can further include alumina added in an amount between 0.001 wt. % and 8 wt. % on the zirconia. The catalyst of this invention obtains a dehydrogenation conversion rate where the conversion due to the zirconia is greater than 50% of the conversion, and preferably the dehydrogenation selectivity due to the zirconia is greater than 80%.

The present invention is a catalyst comprising: an inner core comprising a first refractory inorganic component; and an outer layer comprising zirconia. The catalyst can further include a stabilizing metal oxide selected from the group consisting of scandium, yttrium, lanthanum, cerium, calcium, magnesium, silicon, and mixtures thereof, wherein the metal oxide is in a concentration between 0.001 wt. % and 10 wt. %. The first refractory inorganic component is selected from the group consisting of alpha alumina, theta alumina, silicon carbide, metals, cordierite, titania and mixtures thereof. Preferably, the first refractory inorganic component is cordierite, and the first refractory component is treated to be inert. The outer layer has a thickness between 50 and 300 micrometers. The catalyst of this invention obtains a dehydrogenation conversion rate where the conversion due to the zirconia is greater than 80% of the conversion, and preferably the dehydrogenation selectivity due to the zirconia is greater than 90%.

The invention is a process for the dehydrogenation of a paraffin stream from the $C_3$ to $C_{20}$ range, and particularly $C_3$ to $C_4$ paraffins, comprising: contacting the paraffin stream in the absence of oxygen with a zirconia catalyst for a contact time of less than 2 hours, thereby generating a product stream comprising olefins; and recovering the olefins. The paraffin is selected from the group consisting of a $C_2$-$C_{20}$ straight-chained or branched linear paraffin, and a $C_3$-$C_{20}$ cycloparaffin. The process includes a contact time for the paraffin stream in the absence of oxygen with a zirconia catalyst is less then 30 minutes. The dehydrogenation is carried out at a temperature between about 200° C. and about 650° C., in a transport reactor or a fluidized bed reactor. The zirconia catalyst in the process is stabilized with a metal oxide wherein the metal is selected from the group consisting of scandium, yttrium, lanthanum, cerium, actinium, calcium, magnesium, silicon, and mixtures thereof, thereby generating a product stream comprising olefins. The metal in the metal oxide for stabilization of the catalyst is selected from the group consisting of yttrium, lanthanum, cerium and mixtures thereof. One metal oxide for stabilization is yttrium oxide and is an amount between 0 wt. % and 10 wt % of the catalyst, with the amount being preferred between 0.1 wt. % and 10 wt. % of the catalyst, and between 1 wt. % and 8 wt. % of the catalyst. The process can further comprise the regeneration of the catalyst by exposing the catalyst to air at a temperature between about 450° C. and about 750° C. for a period of time between about 15 minutes and about 4 hours.

The invention includes a reforming process which comprises passing a reforming feedstream to a reforming reaction zone containing a reforming catalyst and operated at reforming conditions to generate a reforming zone effluent, wherein the reforming catalyst comprises zirconia stabilized with a metal oxide. The metal in the metal oxide for stabilization of the catalyst is selected from the group consisting of scandium, yttrium, lanthanum, cerium, actinium, calcium, magnesium, silicon and mixtures thereof. The feedstream can be a naphtha feedstream, and reforming conditions include a temperature between 200° C. and 600° C., a pressure between 100 kPa and 20 MPa, a liquid hourly space velocity between 0.1 and 40 hr$^{-1}$, and a mole ratio of hydrogen to hydrocarbon feed between 0.1 and 20. The reforming process comprises dehydrogenating paraffins to aromatics can include using a second catalyst comprising an elemental metal on an inorganic refractory support. The elemental metal is selected from the IUPAC Group 14 and is in an amount between 0.01 and 5 wt. % of the second catalyst. The second metal can be tin, germanium, or a mixture of tin and germanium. The second catalyst can include an elemental metal from the IUPAC Group 10, in an amount between 0.01 and 2 wt. % of the second catalyst.

One of the issues in the catalytic dehydrogenation of hydrocarbons, is the rate of coking of the catalyst. The catalyst can coke up rapidly, and this has often controlled the choice of catalyst, especially the addition of catalytic metals on support. Coking shortens the process time and degrades catalyst performance. With the zirconia catalyst, the coking exists, but is not important. The process has a short catalyst residence time in the reactor, with a residence time of less than 1 hour, preferably less than 30 minutes, more preferably less than 15 minutes, and most preferably less than 10 minutes. By having a short residence time, the catalyst can accumulate coke, but is removed before significant coking occurs. The catalyst is recycled to remove the coke from the catalyst in a continuous process, and the de-coked catalyst is recycled to the reactor.

The coking of the catalyst during the process is partly controlled by the presence of a hydrogen atmosphere during the process, where the hydrogen to hydrocarbon ratio is greater than 1 and typically greater than 2. Although hydrogen is generated, the hydrogen is present to inhibit coking and maintain the activity of the catalyst. With the present invention, the hydrogen to hydrocarbon ratio can be substantially reduced, and is less than 1, with a preferred ratio less of than 0.6, with a more preferred ratio of less than 0.5.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A continuous process for dehydrogenation of a paraffin stream comprising:
    contacting the paraffin stream in the absence of oxygen with a catalyst comprising a catalytically effective amount of zirconia, wherein the zirconia has a predominantly tetragonal structure and is essentially free of catalytic metals, for dehydrogenating a paraffin stream for a catalyst residence time of less than 30 minutes, thereby generating a product stream comprising olefins, and wherein the reaction is operated with a moisture content of less than 3000 ppm water;
    regenerating the catalyst, wherein the catalyst is regenerated by exposing the catalyst to air, at a temperature between about 450° C. and about 750° C. for a period of time between about 5 minutes and about 30 minutes; and recovering the olefins.

2. The process of claim 1 wherein the catalyst is stabilized with a metal oxide wherein the metal is selected from the group consisting of scandium, yttrium, lanthanum, cerium, actinium, calcium, magnesium, silicon, and mixtures thereof, thereby generating a product stream comprising olefins.

3. The process of claim 2 wherein a metal in the metal oxide for stabilization of the catalyst is selected from the group consisting of yttrium, lanthanum, cerium and mixtures thereof.

4. The process of claim 3 wherein the metal in the metal oxide for stabilization of the catalyst is yttrium, and the yttrium oxide is up to 15 wt % of the catalyst.

5. The process of claim 1 wherein the catalyst further includes a binder or filler material, and the binder or filler material comprises between 20% and 80% of the catalyst by weight.

6. The process of claim 2 wherein the metal oxide for stabilization is up to 15 wt. % of the catalyst.

7. The process of claim 6 wherein the metal oxide for stabilization is up to 8 wt. % of the catalyst.

8. The process of claim 1 wherein the paraffin stream comprises from the C3 to C20 range.

9. The process of claim 8 wherein the paraffin stream comprises propane, n-butane, and iso-butane.

10. The process of claim 1 wherein the dehydrogenation is carried out at a temperature between about 200° C. and about 650° C.

11. The process of claim 1 wherein the dehydrogenation reaction takes place in a fluidized bed.

12. The process of claim 1 further comprising passing the zirconia catalyst to a regeneration unit.

13. The process of claim 1 wherein the zirconia catalyst comprises a layered structure, having an inert inner core, and an outer layer of zirconia.

14. The process of claim 1 wherein the catalyst is essentially free of a metal from IUPAC Groups 9-10.

15. The process of claim 1 wherein the catalyst is essentially free of a metal from IUPAC Groups 6 and 9-10.

16. The process of claim 1 wherein the catalyst is essentially free of platinum.

17. The process of claim 1 wherein a dehydrogenation conversion due to the zirconia is greater than 50% of the conversion.

18. The process of claim 1 wherein a dehydrogenation conversion due to the zirconia is greater than 80% of the conversion.

* * * * *